US006352737B1

(12) United States Patent
Dolhaine et al.

(10) Patent No.: US 6,352,737 B1
(45) Date of Patent: Mar. 5, 2002

(54) USE OF NANOSCALE STEROLS AND STEROL ESTERS

(75) Inventors: Hans Dolhaine, Glehn; Christian Kropf; Peter Christophliemk, both of Duesseldorf; Bernd Fabry, Korschenbroich, all of (DE); Manfred Biermann, Cincinnati, OH (US); Christine Schroeder, Duesseldorf (DE)

(73) Assignee: Cognis Deutschland GmbH, Duesseldorf (DE)

( * ) Notice: Subject to any disclaimer, the term of this patent is extended or adjusted under 35 U.S.C. 154(b) by 0 days.

(21) Appl. No.: 09/597,499

(22) Filed: Jun. 20, 2000

Related U.S. Application Data

(60) Provisional application No. 60/141,154, filed on Jun. 25, 1999.

(51) Int. Cl.⁷ .............................. A23D 9/007; C12J 9/00
(52) U.S. Cl. ........................ 426/611; 552/544; 552/545; 552/547; 514/182; 514/562
(58) Field of Search .......................... 426/611; 552/544, 552/545, 547; 514/170, 171, 182, 562

(56) References Cited

U.S. PATENT DOCUMENTS

| | | | |
|---|---|---|---|
| 3,089,939 A | | 5/1963 | Dunlap et al. |
| 3,203,862 A | | 8/1965 | Jones |
| 3,881,005 A | * | 4/1975 | Thakkar et al. ............... 424/238 |
| 4,160,850 A | * | 7/1979 | Hallstrom et al. ........... 426/601 |
| 4,195,084 A | * | 3/1980 | Ong ............................ 424/238 |
| 6,087,353 A | * | 7/2000 | Stewart et al. ............... 514/182 |
| 5,932,562 A | * | 8/2000 | Ostlund, Jr. ................. 514/78 |
| 6,242,001 B1 | * | 6/2001 | Bruce et al. ................. 424/464 |

FOREIGN PATENT DOCUMENTS

| | | |
|---|---|---|
| DE | 2 035 069 | 1/1971 |
| DE | 197 00 796 A1 | 6/1998 |
| EP | 0 195 311 | 9/1986 |
| WO | WO 92/19640 | 11/1992 |

OTHER PUBLICATIONS

Wachter, et al., "Phytosterole—pflanzliche Wirkstoffe in der Kosmetik", Parfumerie und Kosmetik, 75, Nov., 1994, pp. 755–758 & 761.
Wachter, et al., "Phytosterols", Cosmetics & Toiletries, 110, Jul., 1995, pp. 72–74, 76, 78, 80, 82.
Peterson, et al., "Dietary Constituents Affecting Plasma And Liver Cholesterol In Cholesterol–Fed Chicks", J. Nutrit., 50, (1953), pp. 191–201.
Meyer, et al., "Comparative Particle Size Measurements In Lab–Scale Nanoparticle Production Processes", World Congress on Particle Technology 3, Brighton, 1998, pp. 1–10.

* cited by examiner

*Primary Examiner*—Carolyn Paden
(74) *Attorney, Agent, or Firm*—John E. Drach; Aaron R. Ettelman

(57) ABSTRACT

The invention relates to the use of nanoscale sterols and/or sterol esters with particle diameters of 10 to 300 nm as food additives and as active substances for the production of hypocholesterolemic agents. The particular fineness of the particles promotes more rapid absorption by the blood serum after oral ingestion by comparison with conventional sterols and sterol esters.

20 Claims, No Drawings

USE OF NANOSCALE STEROLS AND STEROL ESTERS

CROSS-REFERENCE TO RELATED APPLICATIONS

This application claims priority, under 35 U.S.C. §119(e), of U.S. Provisional Patent Application No. 60/141,154, filed on Jun. 25, 1999, the entire contents of which are hereby incorporated by reference.

BACKGROUND OF THE INVENTION

Sterols and sterol esters are important raw materials both for cosmetics and pharmaceutical products and for the food industry. For example, it is known that sterols, especially vegetable representatives ("phytosterols"), are incorporated in the basal membrane of the skin and pass to the skin surface through the differentiation of the skin cells. This would explain the caring and protecting effect of phytosterols in skin cosmetics. The topical application of sterols also leads to an increased skin moisture level and to an increased lipid content. This improves the desquamation behavior of the skin and reduces erythemas which may be present. Generic discussions regarding properties of certain sterols and sterol esters used in cosmetics have been published, (R. Wachter, *Parf. Kosm.*, Vol. 75, p. 755 (1994) and R. Wachter, *Cosm. Toil.*, Vol. 110, p. 72 (1995)).

Another important property of phytosterols and, above all, of phytosterol esters is their hypocholesterolemic effect, i.e., their ability after oral ingestion, for example as a margarine additive, to significantly reduce cholesterol levels in the blood. This property was described as long ago as 1953 (Peterson, et al., *J. Nutrit.* Vol. 50, p. 191 (1953)). U.S. Pat. Nos. 3,089,939 and 3,203,862, in addition to German Patent Publication No. DE 20 35 069 (Procter & Gamble), point in the same direction. The active substances are normally added to cooking oils or edible oils and are then taken up through the food. However, the quantities used are generally small and are normally below 0.5% by weight, to prevent the edible oils from clouding or the sterols from precipitating when water is added. The incorporation of sitostanol esters in margarine, butter, mayonnaise, salad creams and the like to reduce the blood cholesterol content is proposed in International Patent Publication No. WO 92/19640 (Raision). Reference is also made in this connection to German Patent Publication No. DE-A1 197 00 796 (Henkel).

The effect of sterols and sterol esters is usually associated with the rate at which the compounds are absorbed. So far as the substances available at present are concerned, there is considerable potential for improvement in this regard. Thus, there is a need in the art to accelerate the absorption of orally administered sterols and sterol esters.

BRIEF SUMMARY OF THE INVENTION

Accordingly, the present invention is directed to orally administered sterols and sterol esters in new forms having accelerated absorption. The present invention relates to the use of nanoscale sterols and/or sterol esters with particle diameters of 10 to 300 nm as food additives and as active substances for the production of hypocholesterolemic agents.

It has surprisingly been found that the absorption and hypocholesterolemic effect of sterols and sterol esters, particularly those based on vegetable raw materials, can be significantly increased if they are present in the form of nanoparticles, i.e. particles with a mean diameter of 10 to 300 and preferably 50 to 150 nm. There are two embodiments, namely the direct incorporation of the nanoparticles in the foods and the encapsulation of the particles for separate oral ingestion. The invention also includes the observation that the nanoscale sterols and sterol esters have improved solubility or dispersibility so that even larger quantities can now be clearly and permanently incorporated, for example in edible oils.

DETAILED DESCRIPTION OF THE INVENTION

Sterols (also known as stenols) are animal or vegetable steroids which only contain a hydroxyl group but no other functional groups at C-3. In general, sterols contain 27 to 30 carbon atoms and one double bond in the 5/6 position and occasionally in the 7/8, 8/9 or other positions. Besides these unsaturated species, other sterols are the saturated compounds obtainable by hydrogenation which are known as stanols and which are also encompassed by the present invention. One example of a suitable animal sterol is cholesterol. Typical examples of suitable phytosterols, which are preferred from the applicational point of view, are ergosterols, campesterols, stigmasterols, brassicasterols and, preferably, sitosterols or sitostanols and, more particularly, β-sitosterols or β-sitostanols. Besides the phytosterols mentioned, their esters are preferably used. The acid component of the ester may go back to carboxylic acids corresponding to formula (I):

$$R^1CO-OH \qquad (I)$$

in which $R^1CO$ is an aliphatic, linear or branched acyl group containing 2 to 22 carbon atoms and 0 and/or 1, 2 or 3 double bonds. Typical examples are acetic acid, propionic acid, butyric acid, valeric acid, caproic acid, caprylic acid, 2-ethyl hexanoic acid, capric acid, lauric acid, isotridecanoic acid, myristic acid, palmitic acid, palmitoleic acid, stearic acid, isostearic acid, oleic acid, elaidic acid, petroselic acid, linoleic acid, conjugated linoleic acid (CLA), linolenic acid, elaeosteric acid, arachic acid, gadoleic acid, behenic acid and erucic acid and the technical mixtures thereof obtained, for example, in the pressure hydrolysis of natural fats and oils, in the reduction of aldehydes from Roelen's oxosynthesis or as monomer fraction in the dimerization of unsaturated fatty acids. Technical fatty acids containing 12 to 18 carbon atoms, for example cocofatty acid, palm oil fatty acid, palm kernel oil fatty acid or tallow fatty acid, are preferred. It is particularly preferred to use esters of β-sitosterol or β-sitostanol with fatty acids containing 12 to 18 carbon atoms. These esters may be prepared both by direct esterification of the phytosterols with the fatty acids or by transesterification with fatty acid lower alkyl esters or triglycerides in the presence of suitable catalysts, for example sodium ethylate or, more particularly, enzymes, such as is described in European Patent Publication No. EP-A2 0195311 (Yoshikawa).

Production of nanoparticles

One process for the production of nanoparticles by rapid expansion of supercritical solutions (RESS) is known from the article by S. Chihlar, M. Türk and K. Schaber in *Proceedings World Congress on Particle Technology* 3, Brighton, 1998. To prevent the nanoparticles from agglomerating, it is advisable to add the nanoparticles either immediately after production of the foods or to dissolve the starting materials in the presence of suitable, i.e. above all toxicologically safe, protective colloids or emulsifiers and/or to expand the critical solutions into aqueous and/or alcoholic solutions of the protective colloids or emulsifiers which may in turn contain redissolved emulsifiers and/or protective colloids. Suitable protective colloids are, for example, gelatine, chitosan, casein, gum arabic, lysalbinic acid, starch and polymers, such as polyvinyl alcohols, polyvinyl pyrrolidones, polyalkylene glycols and polyacrylates. Accordingly, the nanoscale sterols and/or sterol esters preferably used are those which are surrounded by a toxicologically safe protective colloid and/or an emulsifier. Gelatine, chitosan or mixtures thereof are preferably used. The protective colloids or emulsifiers are normally used in quantities of 0.1 to 20% by weight and preferably in quantities of 5 to 15% by weight, based on the sterols or sterol esters. Another suitable process for the production of nanoscale particles is the evaporation technique. Here, the starting materials are first dissolved in a suitable organic solvent (for example alkanes, vegetable oils, ethers, esters, ketones, acetals and the like). The resulting solutions are then introduced into water or another non-solvent, optionally in the presence of a surface-active compound dissolved therein, in such a way that the nanoparticles are precipitated by the homogenization of the two immiscible solvents, the organic solvent preferably evaporating. O/w emulsions or o/w microemulsions may be used instead of an aqueous solution. The emulsifiers and protective colloids mentioned at the beginning may be used as the surface-active compounds. Another method for the production of nanoparticles is the so-called GAS process (gas anti-solvent recrystallization). This process uses a highly compressed gas or supercritical fluid (for example carbon dioxide) as non-solvent for the crystallization of dissolved substances. The compressed gas phase is introduced into the primary solution of the starting materials and absorbed therein so that there is an increase in the liquid volume and a reduction in solubility and fine particles are precipitated. The PCA process (precipitation with a compressed fluid anti-solvent) is equally suitable. In this process, the primary solution of the starting materials is introduced into a supercritical fluid which results in the formation of very fine droplets in which diffusion processes take place so that very fine particles are precipitated. In the PGSS process (particles from gas saturated solutions), the starting materials are melted by the introduction of gas under pressure (for example carbon dioxide or propane). Temperature and pressure reach near- or super-critical conditions. The gas phase dissolves in the solid and lowers the melting temperature, the viscosity and the surface tension. On expansion through a nozzle, very fine particles are formed as a result of cooling effects.

The particular fineness of the particles promotes more rapid absorption by the blood serum after oral ingestion by comparison with conventional sterols and sterol esters. Besides the in situ encapsulation of the nanoparticles, the substances may also be dissolved or dispersed in normal foods such as, for example, butter, margarine, diet foods, frying oils, edible oils, mayonnaises, salad dressings, cocoa products, sausage and the like. The quantity in which the nanoscale compounds are used is normally of the order of 0.01 to 5% by weight, preferably between 0.1 and 2% by weight and more preferably from 0.5 to 1% by weight, based on the food.

The present invention will now be illustrated in more detail by reference to the following specific, non-limiting examples.

EXAMPLES 1 TO 5

To prepare the nanoscale sterols and sterol esters (Examples 1 to 5), carbon dioxide was taken from a reservoir under a constant pressure of 60 bar and purified in a column with an active carbon packing and a molecular sieve packing. After liquefaction, the $CO_2$ was compressed to the required supercritical pressure p by meand of a diaphragm pump at a constant delivery rate of 3.5 l/h. The solvent was then brought to the necessary temperature T1 in a preheater and introduced into an extraction column (steel, 400 ml) which had been charged with the sterol or sterol ester. resulting supercritical, i.e., fluid, mixture was sprayed through a laser-drawn nozzle (length 830 μm, diameter 45 μm) at a temperature T2 into a Plexiglas expansion chamber which contained a 4% by weight aqueous dispersion of a protective colloid. The fluid medium evaporated, leaving the nanoparticles dispersed in the protective colloid behind.

EXAMPLE 6

To produce the nanoparticles of Example 6, a 1% by weight solution of phytosterol in acetone was added dropwise to a 4% by weight aqueous dispersion of a mixture of gelatine and chitosan with vigorous stirring at 40° C. under a reduced pressure of 40 mbar. The evaporating solvent was condensed in a cold trap while the dispersion containing the nanoparticles remained behind. The process conditions and the mean partical size range (as determined photometrically by the 3-WEM method for Examples 1 to 5 and by laser scattering for Example 6) are shown in Table 1 below.

TABLE 1

| | | | Nanoparticles | | | | |
| Ex. | Sterol/ Sterol Ester | Solv. | p (bar) | T1 (° C.) | T2 (° C.) | Protective Colloid | PSR (nm) |
| --- | --- | --- | --- | --- | --- | --- | --- |
| 1 | Phytosterol* | $CO_2$ | 200 | 80 | 175 | Gelatine | 60–135 |
| 2 | Phytosterol* | $CO_2$ | 180 | 70 | 160 | Gelatine | 75–125 |
| 3 | β-Sitostanol | $CO_2$ | 200 | 85 | 180 | Gelatine | 75–130 |
| 4 | β-Sitostenyl laurate | $CO_2$ | 200 | 85 | 175 | Chitosan | 55–140 |
| 5 | β-Sitostanyl stearate | $CO_2$ | 200 | 85 | 175 | Gelatine/ chitosan (1:1) | 60–150 |
| 6 | Phytosterol* | — | — | — | — | Gelatine/ chitosan (1:1) | 65–150 |

*58.1% by weight β-sitosterol, 29.8% by weight campesterol, 4.5% by weight stigmasterol; 3.8% by weight tocopherol; 0.4% by weight cholesterol; 0.3% by weight squalane; unsaponifiables to 100.

HYPOCHOLESTEROLEMIC EFFECT EXAMPLES

Gelatine capsules (weight ca. 1.5 g) containing 5% by weight β-sitostanol or β-sitostanolester (nanoparticles encapsulated in a gelatine or chitosan matrix and non-nanoscale commercial products) and 0.5% by weight of radioactively marked cholesterol were prepared. To study the hypocholesterolemic effect, male rats (individual weight ca.200 g) were allowed no food overnight. The next day, a size-reduced gelatine capsule was inserted into each test animal via a stomach probe together with a little water containing sodium chloride. After 3, 6, 12, 24 and 48 h, blood was taken from the animals and the content of radioactive cholesterol was determined. The results, which represent the mean value of the measurements of 10 test animals, are set out in Table 2. The figures relating to the reduction in radioactivity are based on a blank group of test animals which were only given gelatine capsules containing 20% by weight of vitamin E and a corresponding quantity of radioactively marked cholesterol. Examples 1 and 2 correspond to the invention, Examples C1 and C2 are intended for comparison.

TABLE 2

Hypocholesterolemic effect

| | | Radioactivity [%-rel.] | | | | |
|---|---|---|---|---|---|---|
| Ex. | Phytosterol(ester) | After 3 h | After 6 h | After 12 h | After 24 h | After 48 h |
| C1 | β-Sitostanol* | 93 | 83 | 75 | 50 | 32 |
| C2 | β-Sitostanyl stearate* | 90 | 80 | 71 | 44 | 26 |
| 1 | Nano-β-sitostanol** | 88 | 77 | 69 | 44 | 27 |
| 2 | Nano-β-sitostanyl stearate*** | 85 | 74 | 66 | 37 | 21 |

*commercial products
**acc. to Production Example 3
***acc. to Production Example 5

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. A hypocholesteremic agent comprising at least one active substance selected from the group consisting of nanoscale sterols and nanoscale sterol esters, wherein the at least one active substance has a mean particle diameter value of from about 10 to about 300 nm.

2. The hypocholesteremic agent according to claim 1, wherein the at least one active substance has a mean particle diameter value of from about 50 to about 150 nm.

3. The hypocholesteremic agent according to claim 1, wherein the at least one active substance is selected from the group consisting of nanoscale phytosterols and nanoscale phytosterol esters.

4. The hypocholesteremic agent according to claim 1, wherein the at least one active substance is selected from the group consisting of nanoscale sitosterols and nanoscale sitosterol esters.

5. The hypocholesteremic agent according to claim 1, further comprising a second component selected from the group consisting of protective colloids and emulsifiers.

6. The hypocholesteremic agent according to claim 5, wherein the second component is present in an amount of from about 0.1 to about 20 % by weight, based on the at least one active substance.

7. The hypocholesteremic agent according to claim 5, wherein the second component comprises a protective colloid selected from the group consisting of gelatin and chitosan.

8. The hypocholesteremic agent according to claim 1, further comprising a protective colloid selected from the group consisting of gelatin and chitosan, wherein the second component is present in an amount of from about 0.1 to about 20 % by weight, based on the at least one active substance, and wherein the at least one active substance is selected from the group consisting of nanoscale sitosterols and nanoscale sitosterol esters.

9. A hypocholesteremic agent comprising at least one active substance selected from the group consisting of nanoscale sterols and nanoscale sterol esters, wherein the at least one active substance is prepared by mixing the at least one active substance with a suitable solvent under super-critical or near-critical conditions to provide a mixture; expanding the mixture and removing the solvent.

10. The hypocholesteremic agent according to claim 9, wherein the mixture is expanded through a nozzle into a vacuum.

11. A edible composition comprising a food product and a hypocholesteremic agent, the hypocholesteremic agent comprising at least one active substance selected from the group consisting of nanoscale sterols and nanoscale sterol esters, wherein the at least one active substance has a mean particle diameter value of from about 10 to about 300 nm.

12. The edible composition according to claim 11, wherein the food product is selected from the group consisting of butters, margarines, diet foods, frying oils, edible oils, mayonnaises, salad dressings, cocoa products, and sausage.

13. The edible composition according to claim 11, wherein the at least one active substance is present in an amount of from about 0.01 to about 5 % by weight, based on the amount of the food product.

14. The edible composition according to claim 11, wherein the at least one active substance is present in an amount of from about 0.5 to about 1 % by weight, based on the amount of the food product.

15. The edible composition according to claim 11, wherein the at least one active substance has a mean particle diameter value of from about 50 to about 150nm.

16. The edible composition according to claim 11, wherein the at least one active substance is selected from the group consisting of nanoscale phytosterols and nanoscale phytosterol esters.

17. The edible composition according to claim 11, wherein the at least one active substance is selected from the group consisting of nanoscale sitosterols and nanoscale sitosterol esters.

18. The edible composition according to claim 11, further comprising a second component selected from the group consisting of protective colloids and emulsifiers.

19. The edible composition according to claim 11, wherein the second component is present in an amount of from about 0.1 to about 20 % by weight, based on the at least one active substance.

20. The edible composition according to claim 11, wherein the second component comprises a protective colloid selected from the group consisting of gelatin and chitosan.

* * * * *